(12) United States Patent
Hansen (10) Patent No.: US 11,684,286 B2
(45) Date of Patent: Jun. 27, 2023

(54) PORTABLE SPIROMETER

(71) Applicants: MOVE FINANCE HOLDING ApS, Birkerød (DK); UDVIRK v/Jørgen Ole Kjær, Birkerød (DK)

(72) Inventor: Martin Bo Hansen, Søborg (DK)

(73) Assignees: MOVE FINANCE HOLDING ApS, Birkerød (DK); UDVIRK V/JØRGEN OLE KJÆR, Birkerød (DK)

( * ) Notice: Subject to any disclaimer, the term of this patent is extended or adjusted under 35 U.S.C. 154(b) by 309 days.

(21) Appl. No.: 16/956,072

(22) PCT Filed: Dec. 20, 2018

(86) PCT No.: PCT/EP2018/086244
§ 371 (c)(1),
(2) Date: Jun. 19, 2020

(87) PCT Pub. No.: WO2019/122156
PCT Pub. Date: Jun. 27, 2019

(65) Prior Publication Data
US 2021/0007628 A1 Jan. 14, 2021

(30) Foreign Application Priority Data
Dec. 21, 2017 (EP) .................... 17209599

(51) Int. Cl.
*A61B 5/087* (2006.01)
*A61B 5/097* (2006.01)

(52) U.S. Cl.
CPC ............ *A61B 5/0878* (2013.01); *A61B 5/097* (2013.01); *A61B 2562/028* (2013.01); *A61B 2562/0247* (2013.01)

(58) Field of Classification Search
CPC ....... A61B 5/087; A61B 5/0878; A61B 5/097; A61B 2562/047; A61B 2562/028; G01N 33/497
See application file for complete search history.

(56) References Cited

U.S. PATENT DOCUMENTS

2008/0038207 A1 2/2008 Edwards et al.
2015/0164373 A1* 6/2015 Davis ............... A61B 5/0871
                                                        600/529

(Continued)

FOREIGN PATENT DOCUMENTS

EP      0552916 A1 *  7/1993
WO      2014/179083    11/2014
WO      WO-2015193475 A1 * 12/2015 ........... A61B 5/0022

OTHER PUBLICATIONS

International Search Report and Written Opinion of the ISA for PCT/EP2018/086244 dated Mar. 26, 2019, 14 pages.
Search Report for EP17209599.4 dated Jun. 13, 2018, 8 pages.

*Primary Examiner* — Herbert K Roberts
(74) *Attorney, Agent, or Firm* — Nixon & Vanderhye P.C.

(57) ABSTRACT

The present invention relates to a portable spirometer, comprising a housing and a mouthpiece being releasably connected to said housing, wherein the housing encloses a sensor unit being in fluid communication with a flow channel receiving part of a flow of exhaled or inhaled air from a main flow channel of the mouthpiece when connected to said housing, whereby the sensor unit is configured to measure one or more characteristics of part of the flow of exhaled or inhaled air passed to the sensor unit via the mouthpiece, characterised in that said sensor unit comprises at least one digital differential pressure sensor comprising a heating element and a temperature sensor arranged upstream of the heating element and a reference temperature sensor arranged downstream of the heating element.

16 Claims, 5 Drawing Sheets

(56) References Cited

U.S. PATENT DOCUMENTS

2015/0250408 A1* 9/2015 Ssenyange .......... G01N 33/0037
  600/532
2016/0345860 A1   12/2016 Wolfe et al.

* cited by examiner

PORTABLE SPIROMETER

This application is the U.S. national phase of International Application No. PCT/EP2018/086244 filed Dec. 20, 2018 which designated the U.S. and claims priority to EP Patent Application No. 17209599.4 filed Dec. 21, 2017, the entire contents of each of which are hereby incorporated by reference.

The present invention relates to a portable spirometer, comprising a housing and a mouthpiece being releasably connected to said housing. Furthermore, the present invention relates to a method of measuring the flow of air being inhaled or exhaled by a user.

A device for measuring the volume of air being expired by the lungs is commonly denoted as a spirometer. Normally, by measuring the air flowing in and out from the lungs, it is possible to detect abnormal ventilation patterns, e.g. obstructive or restrictive, indicating possible lung diseases.

Spirometers are therefore typically provided at health care centres, whereby the patient can perform basic pulmonary function tests which can be evaluated by a medical doctor.

In WO2015/193475 by the same applicant, a portable spirometer is disclosed which allows a user to monitor the physiological pulmonary condition at any given time, independently of the availability at the health care centres. Consequently by using such device, it is possible to perform monitoring at regular intervals, thus increasing the chance of avoiding irreparable damage to the lungs.

As the position of the portable spirometer may vary for different measurements or during one measurement, small deviations in the measured air flow may occur, especially during rapid movements such as shaking etc. Therefore, it would be desirable to provide a portable spirometer having improved accuracy.

It is an object of the present invention to wholly or partly overcome the above disadvantages and drawbacks of the prior art. More specifically, it is an object to provide an improved portable, or hand-held, spirometer which allows for reliable and accurate measurements of the air flow.

The above objects, together with numerous other objects, advantages and features, which will become evident from the below description, are accomplished by a solution in accordance with the present invention by a portable spirometer, comprising a housing and a mouthpiece being releasably connected to said housing, wherein the housing encloses a sensor unit being in fluid communication with a flow channel receiving part of a flow of exhaled or inhaled air from a main flow channel of the mouthpiece when connected to said housing, whereby the sensor unit is configured to measure one or more characteristics of part of the flow of exhaled or inhaled air passed to the sensor unit via the mouthpiece, characterised in that said sensor unit comprises at least one digital differential pressure sensor comprising a heating element, a temperature sensor arranged upstream of the heating element and a reference temperature sensor arranged downstream of the heating element.

The at least one digital differential pressure sensor may be configured to measure thermal flow of the air, and to convert the measured thermal flow to a value representing air flow.

Moreover, the at least one digital differential pressure sensor may be configured to measure a first temperature and a second temperature which are converted to a differential pressure.

Additionally, the reference temperature sensor may measure the temperature of the air after being heated by the heating element.

Further, the heating element, the reference temperature sensor and the temperature sensor may be arranged in series.

Moreover, the heating element, the reference temperature sensor and the temperature sensor may be arranged in a flow channel being in fluid communication with the flow channel receiving part of the flow of exhaled or inhaled air from a main flow channel of the mouthpiece.

In addition, the heating element, the reference temperature sensor and the temperature sensor may be arranged in the same flow channel being in fluid communication with the flow channel receiving part of the flow of exhaled or inhaled air from a main flow channel of the mouthpiece.

Furthermore, the flow channel may be perpendicular to the main flow channel of the mouthpiece.

In addition, said sensor unit may comprise at least two digital differential pressure sensors.

Also, the at least two digital differential pressure sensors may be arranged in parallel.

Furthermore, the at least two digital differential pressure sensors may be arranged in series.

The digital differential pressure sensor may be arranged as part of a microchip.

Further, the heating element, the reference temperature sensor and the temperature sensor of the digital pressure sensor may be arranged in a first air channel arranged in a microchip, where the first air channel has an inlet fluid communication mouthpiece at one side of the microchip and an outlet at the other side of the microchip.

In addition, the first air channel may have the outlet in fluid communication with the surroundings.

Furthermore, the air conduit may form part of a micromachined device, such as a MEMS.

Moreover, the heating element, the reference temperature sensor and the temperature sensor of a first digital differential pressure sensor may be arranged in a first air channel, and the heating element, the reference temperature sensor and the temperature sensor of a second digital differential pressure sensor may be arranged in a second air channel, and the diameter of the first fluid channel may be different from the diameter of the second fluid channel.

A first digital differential sensor may be configured to measure the differential pressure within a first interval, and a second digital differential sensor may be configured to measure the differential pressure within a second interval.

Further, the first and second intervals may be overlapping.

The present invention also relates to a method of measuring the flow of air being inhaled or exhaled by a user, comprising:

blowing air into a mouthpiece being releasably connected to a housing, forwarding part of the air from a main flow channel of the mouthpiece to a flow channel of the housing enclosing a sensor unit being in fluid communication with the main flow channel of the mouthpiece when connected to said housing, and measuring one or more characteristics of the flow of exhaled or inhaled air passed to the sensor unit via the mouthpiece by means of the sensor unit, whereby said sensor unit comprises at least one differential pressure sensor.

Finally, the one or more characteristics of the flow of exhaled or inhaled air may be measured by measuring a first temperature of a part of the flow by the temperature sensor, heating the part of the air having past the temperature sensor by means of the heating element, and measure a second temperature of the part of the flow heated by the heating element by the reference temperature sensor.

The invention and its many advantages will be described in more detail below with reference to the accompanying schematic drawings, which for the purpose of illustration show some non-limiting embodiments and in which.

All the figures are highly schematic and not necessarily to scale, and they show only those parts which are necessary in order to elucidate the invention, other parts being omitted or merely suggested.

Figure 1:
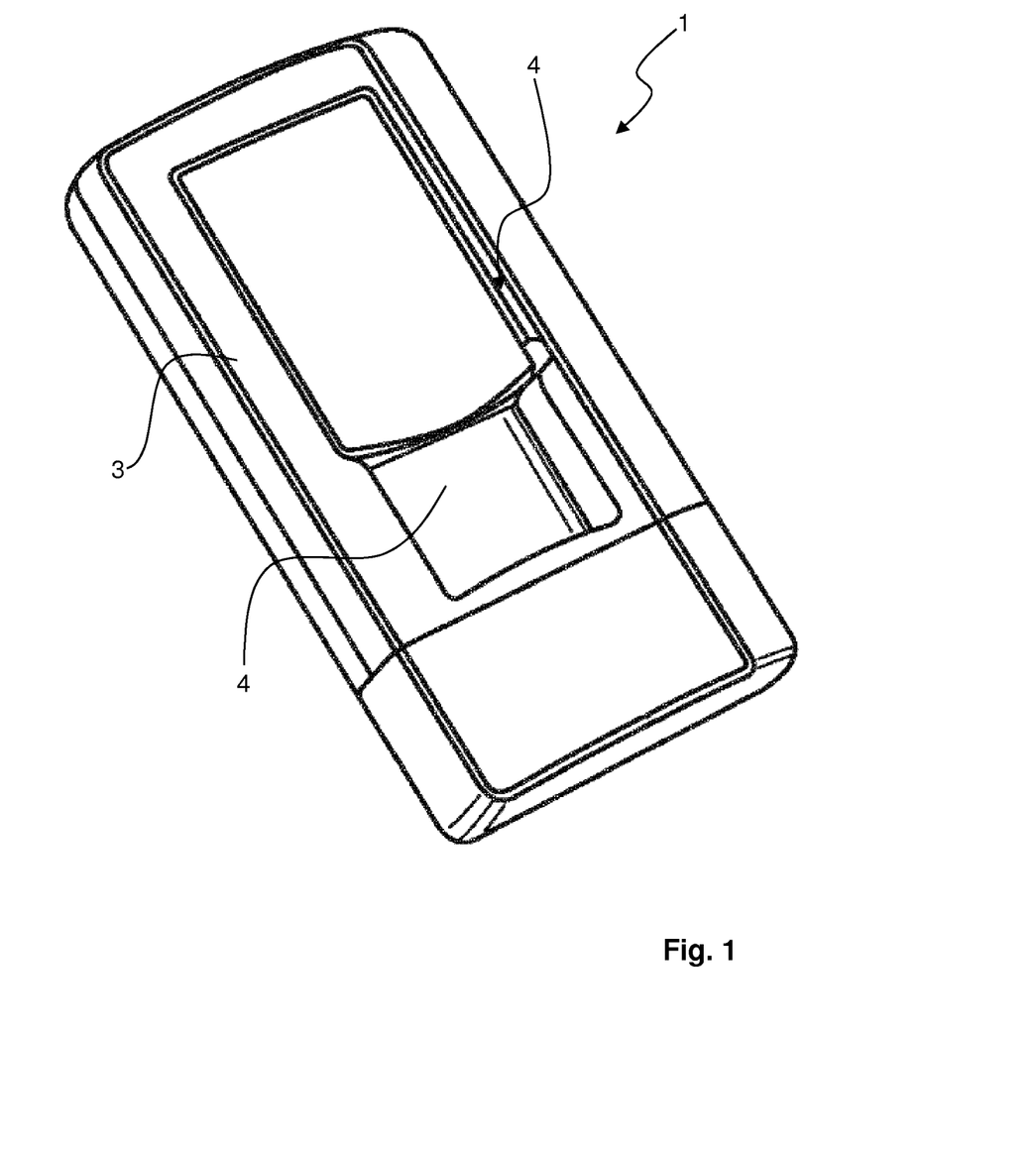
FIG. 1 is an isometric view of a portable spirometer, when arranged in a standby position, according to an embodiment.
Figure 2:
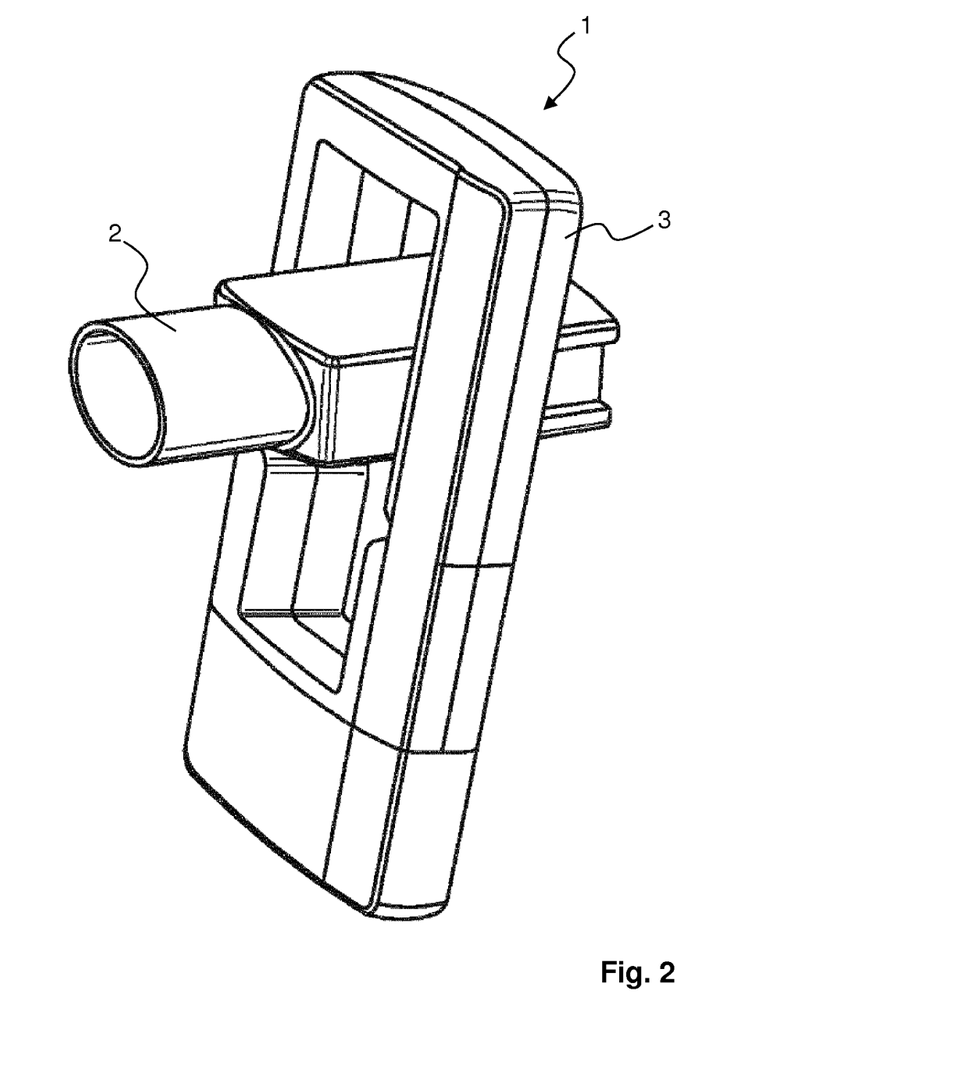
FIG. 2 is an isometric view of the portable spirometer shown in FIG. 1, here arranged in an active position.

A spirometer 1, i.e. a device for monitoring the physiological pulmonary condition of a user, is shown in FIGS. 1 and 2. The spirometer 1 is to be used by a user exhaling air into a mouthpiece 2 or inhaling air through the mouthpiece 2, creating a flow of exhaled air or inhaled air through the mouthpiece 2. One or more characteristics of at least part of said flow of exhaled air or inhaled air is/are to be measured by a sensor unit 10, which will be further described with reference to FIGS. 3-6. The sensor unit 10 is embedded in a housing 3 which forms a means for holding the spirometer 1 by one hand of the user, while the user exhales air or inhales air into the mouthpiece 2.

The mouthpiece 2 is releasably connected to the housing 3 by means of a pivot joint 4. When the mouthpiece 2 is connected to the housing 3, the mouthpiece 2 may be pivoted between a standby position, shown in FIG. 2, and an active position as shown in FIG. 3. When released from the housing 3, the mouthpiece 2 may be cleaned, replaced etc. without the risk of damaging the sensor unit 10.

Figure 3A:
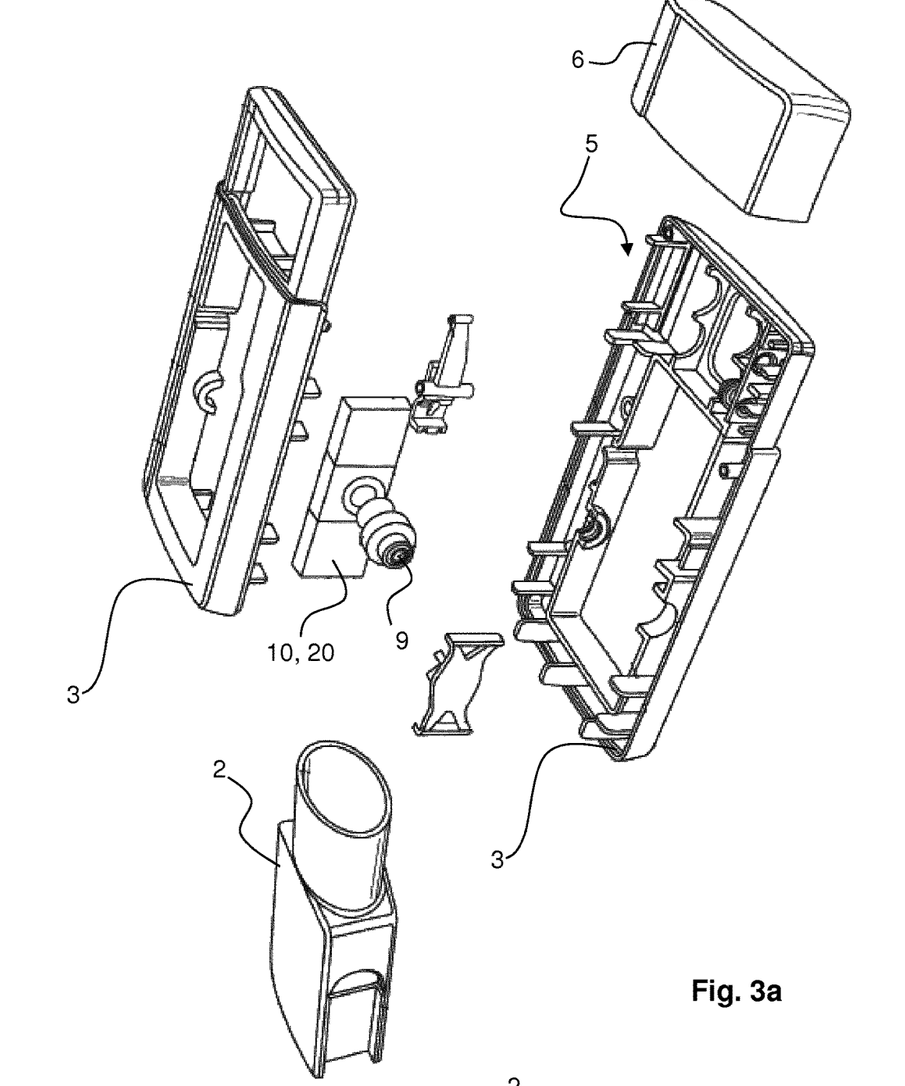
FIG. 3a is an exploded isometric view of the portable spirometer shown in FIGS. 1 and 2.
Figure 3B:
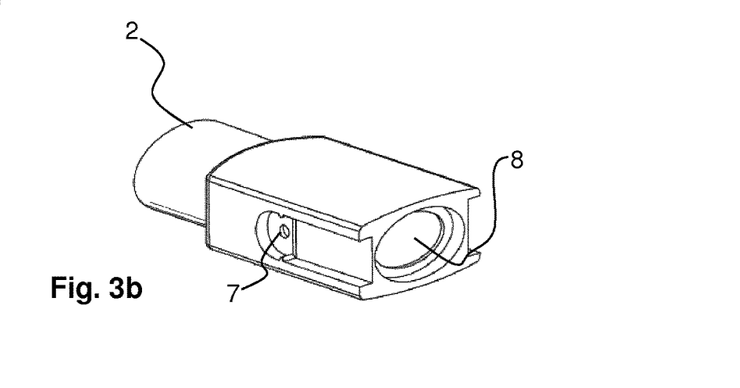
FIG. 3b is an isometric view of a mouthpiece of a portable spirometer according to an embodiment.

A more detailed illustration of the portable spirometer 1 is shown in FIGS. 3a and 3b. As described above, the sensor unit 10 is enclosed inside the housing 10, and receives an air flow from the mouthpiece 2 during use. As is further shown in FIG. 3a, the housing 3 is provided with a battery holder 5 that may be closed by means of a removable cover 6.

The sensor unit 10 forms part of a control unit 20. The control unit 20 provides various functionalities to the portable spirometer 1. For example, the control unit 20 may be configured to detect the position of the mouthpiece 2 relative to the housing 3, and, when a user arranges the mouthpiece 2 in the active position, activates the sensor unit 10 as well as communication means for transmitting measured data to a remote receiving unit (not shown). For this purpose, the control unit 20 may comprise a transmitter for transmitting data of the measurements to a remote data receiver. Data is preferably transmitted via wireless data transmission such as Bluetooth. Data is also preferably transmitted to a mobile or cellular phone, which phone has computer programmes for processing the received data. The mobile or cellular phone may also have hardware and computer programmes for passing on data to other remote data receivers, e.g. made available to a health care provider.

As can be seen in FIG. 3b, the mouthpiece 2 is provided with a flow channel 7 which extends from a main flow channel 8, preferably perpendicularly. As the main flow channel 8 receives the air during inhalation or exhalation, some of the air will flow into the flow channel 7.

The housing 2 is provided with a flow channel 9 which connects with the flow channel 7 of the mouthpiece 2 when the mouthpiece 2 is connected to the housing 3. As air is flowing into the main flow channel 8, part of the flow flows into the flow channel 7 and into the flow channel 9 during use, that air will be guided to flow across the sensor unit 10 which can then measure the air flow. In another embodiment, part of the air flows directly from main flow channel 8 across the sensor unit 10 via only the flow channel 7.

Figure 4:
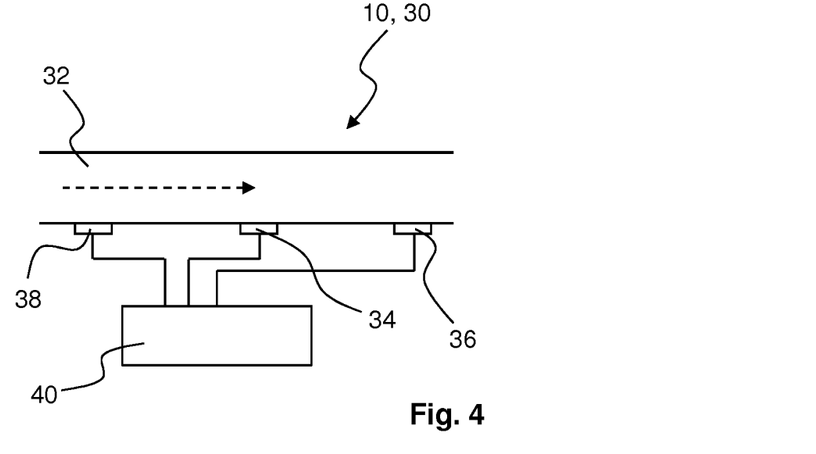
FIG. 4 is a schematic view of a sensor unit for use with a portable spirometer according to an embodiment.

As will be explained in the following, the sensor unit 10 comprises at least one digital differential pressure sensor 30. An example of such digital differential pressure sensor 30 is shown in FIG. 4. The digital differential pressure sensor 30 comprises an air conduit 32 receiving air from the main flow channel 8 via the flow channel 9 or directly from flow channel 7 during use of the portable spirometer 1, and a heating element 34 arranged at the air conduit 32 at a pre-determined position so that upon activation of the heating element 34, the air flowing inside the air conduit 32 will be heated. Hence, the heating element 34 may e.g. be arranged on the outside of the air conduit 32, on the inside of the air conduit 32, or the heating element 34 may form part of the wall of the air conduit 32. The dimension of the air conduit 32 is preferably sub-mm (i.e. less than 1 millimetre), so that the air conduit 32 forms part of a micromachined device, such as a MEMS. A MEMS (microelectromechanical system) can be particularly advantageous, especially since it allows the heating element 34, as well as the air conduit 32, to be manufactured directly onto the electronic chip itself. Improved integration of the sensor unit 10 is thereby achieved. Further, implementing the sensor unit 10 as a MEMS also allows for a very small component, still providing extremely high accuracy and reliability, as well as facilitated design of electronics.

In addition to the heating element 34, the digital differential pressure sensor 30 further comprises a first temperature sensor 36, arranged downstream the heating element 34. Hence, as air is flowing in the direction of the arrow shown in FIG. 4, the air will first pass the heating element 34, whereby the air will be heated. Further downstream in the flow direction, the air will pass the first temperature sensor 36, which measures the temperature of the air flowing across it. The digital differential pressure sensor 30 further comprises a reference temperature sensor 38 which is positioned upstream the heating element 34 and is measuring a temperature of the heated air further downstream in the flow direction. The air will pass first the first temperature sensor 36 and then the heating element and then the temperature sensor 38.

A controller 40, which may be formed integrally with the control unit 20 described above or as a separate digital circuitry, controls the operation of the sensors 36, 38 as well as the heating element 34. During operation, the controller 40 will transmit a control signal to the heating element 34. The control signal may e.g. be an activation current generating heat in a resistance of the heating element 34. The controller 40 further receives input from the temperature sensors 36, 38, whereby the controller 40 is configured to measure the temperature increase of the air flow due to the applied heat, and to convert the measured temperature increase to a corresponding pressure difference. Such conversion is made by using the temperature profile of the air flow, and associating this temperature profile to a corresponding mass flow rate. The mass flow rate is consequently converted to a differential pressure applying Bernoulli's Principle given by the equation:

$$P = \rho/2(Q/A)^2$$

where Q is Volumetric Flow rate; A is Area; P is Pressure, in which P is related to Volumetric Flowrate of the channel (pipe).

Figure 5:
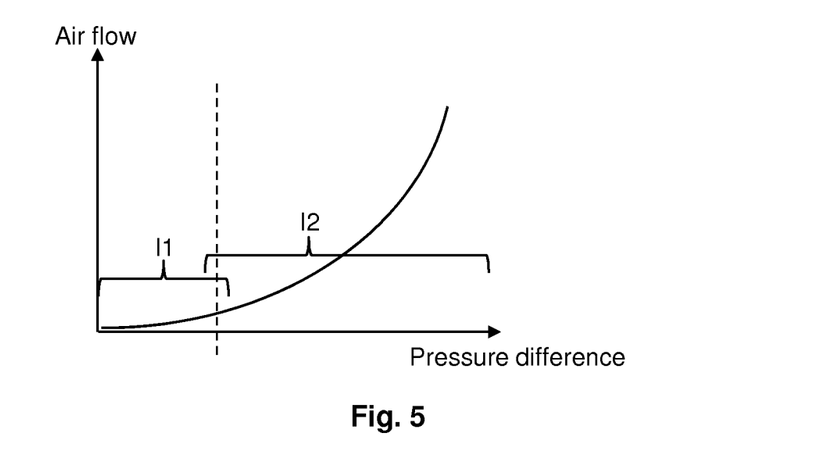
FIG. 5 is a diagram showing the air flow as a function of the pressure.
Figure 6:
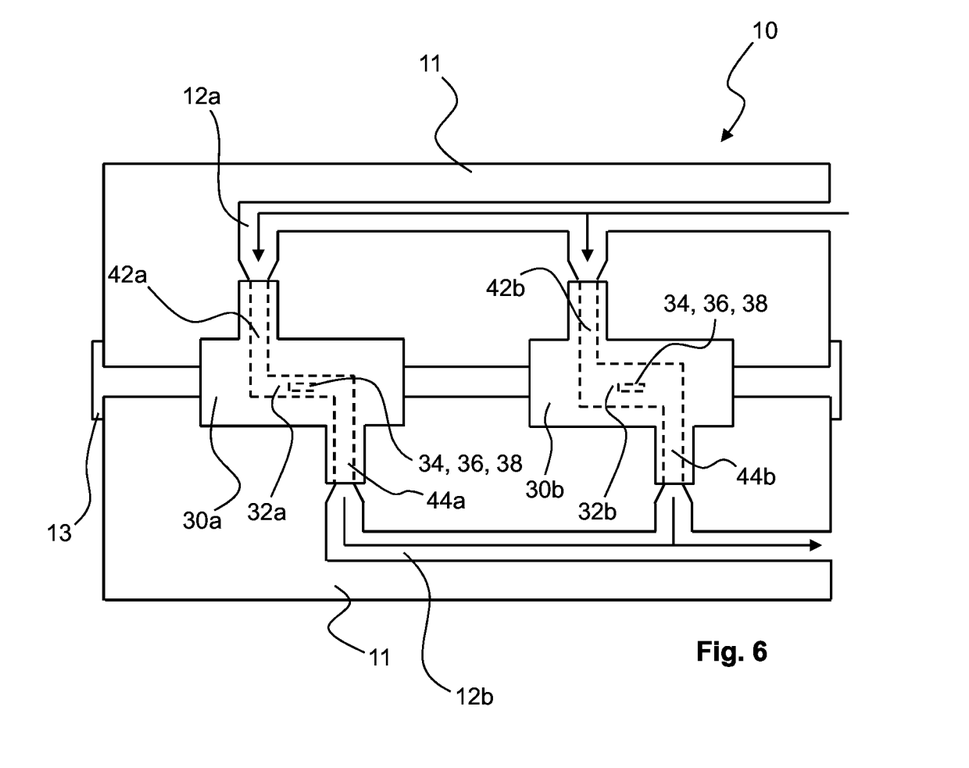
FIG. 6 is a schematic cross-sectional view of a sensor unit for use with a portable spirometer according to an embodiment.

In an embodiment, two digital differential pressure sensors 30a, 30b are included in a common sensor unit 10, as shown in FIG. 6. The use of two or more digital differential pressure sensors 30a, 30b is advantageous for a number of reasons. Now referring to FIG. 5, a diagram showing the air flow as a function of differential pressure is shown. Due to specifications of the hardware, it may be difficult to design a single digital differential pressure sensor 30 to measure accurately in a wide range. Therefore, in practice high resolution and accuracy are normally only guaranteed for a specific differential pressure interval.

In order to overcome this drawback and ensure accurate measurements in the entire possible range, two digital differential pressure sensors 30a, 30b may be designed to measure specific ranges of the differential pressure. As is shown in FIG. 5, the differential pressure range is divided into two sections, or intervals I1, I2. One digital differential pressure sensor 30a (shown in FIG. 6) is configured to measure the differential pressure in the first interval I1, while the second digital differential pressure sensor 30b is configured to measure the differential pressure in the second interval I2. These two intervals I1, I2 are preferably overlapping. This is not only reducing the risk for loosing any data, but it can also provide calibration data so that the two individual digital differential pressure sensors 30a, 30b are matched.

As is clear from FIG. 5, once the differential pressure is measured, conversion to air flow can be performed immediately, e.g. by one or more conversion factors.

In FIG. 6, an example of a sensor unit 10 is shown in cross-section. The sensor unit 10 comprises a sensor unit housing 11, which has an air channel 12a for directing air flowing from the flow channel 9 to the digital differential pressure sensors 30a, 30b, as well as a return channel 12b for directing air flowing from the digital differential pressure sensors 30a, 30b. The air channel 12a is in fluid communication with the air channel 9 or flow channel 7 of the spirometer housing 3 (see FIG. 3a). The sensor unit 10 further comprises a circuit board 13, which carries the controller 40 and necessary electronic components for ensuring reliable operation of the sensor unit 10.

The air channel 12a diverts into a first branch forming an inlet channel for the first digital differential pressure sensor 30a, and a second branch forming an inlet channel for the second digital differential pressure sensor 30b. In a similar manner, the return air channel 12b converges from a first branch forming an outlet channel for the first digital differential pressure sensor 30a, and a second branch forming an outlet channel for the second digital differential pressure sensor 30b. Although the first and second digital differential pressure sensors 30a, 30b are shown to operate in parallel, it would also be possible to arrange the first and second digital differential pressure sensors 30a, 30b in series.

The first digital differential pressure sensor 30a comprises an inlet channel 42a receiving air flow from the air channel 12a of the sensor unit housing 11, and an outlet channel 44a for returning air flow to the air channel 12b of the sensor unit housing 11. An air channel 32a is arranged between the inlet channel 42a and the outlet channel 44a. The air channel 32a is provided with the heating element 34 and the temperature sensor 36, and also the reference temperature sensor 38.

Similarly, the second digital differential pressure sensor 30b comprises an inlet channel 42b receiving air flow from the air channel 12a of the sensor unit housing 11, and an outlet channel 44b for returning air flow to the air channel 12b of the sensor unit housing 11. An air channel 32b is arranged between the inlet channel 42b and the outlet channel 44b. The air channel 32b is provided with the heating element 34 and the temperature sensor 36, and also the reference temperature sensor 38.

The diameter of the air channel 32a of the first digital differential pressure sensor 30a may, in some embodiments, be different from the diameter of the air channel 32b of the second digital differential pressure sensor 30b, i.e. smaller or larger. This provides an advantage in that systematic measurement errors may be identified and corrected for.

The entire sensor unit 30 is preferably provided onto a digital chip, which means that extremely compact packaging of the sensor unit 10 is possible.

Figure 7:
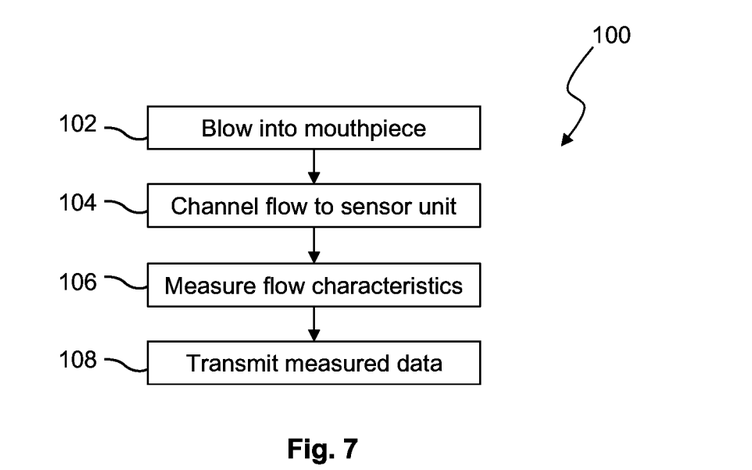
FIG. 7 is a schematic view of a method according to an embodiment.

Now turning to FIG. 7, a method 100 for measuring the flow of air being inhaled or exhaled by a user is schematically shown. The method comprises a first step 102 of providing a flow of air into a mouthpiece 2, preferably by allowing a user to blow into the mouthpiece 2. As explained above, the mouthpiece 2 is preferably releasably connected to a housing 3. In a subsequent step 104, the air flow is forwarded from the mouthpiece 2 to the housing 3 which encloses a sensor unit 10 being in fluid communication with the mouthpiece 2 when connected to said housing 3. In a following step 106, one or more characteristics of the flow of exhaled or inhaled air passed to the sensor unit 10 via the main flow cannel 8 of the mouthpiece 2 and further to the flow channel 7 is measured by means of the sensor unit 10, whereby said sensor unit 10 comprises at least one differential pressure sensor 30. Optionally, in step 108, the measured data is transmitted to a remote receiving unit, such as a mobile phone, a PC, a tablet or the like for evaluation and analysis.

Although the invention has been described in the above in connection with preferred embodiments of the invention, it will be evident for a person skilled in the art that several modifications are conceivable without departing from the invention as defined by the following claims.

The invention claimed is:

1. A portable spirometer, comprising a housing and a mouthpiece being releasably connected to said housing, wherein the housing encloses a sensor unit being in fluid communication with a flow channel in the mouthpiece receiving part of a flow of exhaled or inhaled air from a main flow channel of the mouthpiece when connected to said housing, the sensor unit comprising an air conduit that is separate from the flow channel and the main flow channel and in fluid communication with the flow channel and the main flow channel, wherein the air conduit is configured to receive at least a part of the flow of the exhaled or inhaled air via the mouthpiece, whereby the sensor unit is configured to measure a first measurement of a thermal flow of air flowing in the air conduit, wherein said sensor unit comprises at least a first digital differential pressure sensor comprising:
   a heating element,
   a temperature sensor arranged upstream of the heating element, and
   a reference temperature sensor arranged downstream of the heating element, wherein the portable spirometer is configured to convert the first measurement to a value representing air flow through the main flow channel, and
wherein the first digital differential pressure sensor is configured to measure a first temperature and a second temperature which are converted to a differential pressure.

2. The portable spirometer according to claim 1, wherein the first digital differential pressure sensor is configured to measure thermal flow of the air and to convert the measured thermal flow to the value.

3. The portable spirometer according to claim 1, wherein the reference temperature sensor is configured to measure the temperature of the air after being heated by the heating element.

4. The portable spirometer according to claim 1, wherein the heating element, the reference temperature sensor and the temperature sensor are arranged in series.

5. The portable spirometer according to claim 1, wherein the heating element, the reference temperature sensor and the temperature sensor are arranged in the conduit.

6. The portable spirometer according to claim 1, wherein the flow channel is perpendicular to the main flow channel of the mouthpiece.

7. The portable spirometer according to claim 1, further comprising a second digital differential pressure sensor.

8. The portable spirometer according to claim 7, wherein the first and second digital differential pressure sensors are arranged in parallel.

9. The portable spirometer according to claim 1, wherein the first digital differential pressure sensor is arranged as part of a microchip.

10. The portable spirometer according to claim 1, wherein the heating element, the reference temperature sensor and the temperature sensor of the first digital differential pressure sensor are arranged in the air conduit arranged in a microchip, where the air conduit has an inlet in fluid communication with the mouthpiece at one side of the microchip and an outlet at the other side of the microchip.

11. The portable spirometer according to claim 1, wherein the heating element, the reference temperature sensor and the temperature sensor of the first digital differential pressure sensor are arranged in a first air channel, and a second heating element, a reference temperature sensor and a temperature sensor of a second digital differential pressure sensor are arranged in a second air channel, and wherein the diameter of the first air channel is different from the diameter of the second air channel.

12. The portable spirometer according to claim 7, wherein the first digital differential sensor is configured to measure the differential pressure within a first interval, and the second digital differential sensor is configured to measure the differential pressure within a second interval.

13. The portable spirometer according to claim 12, wherein the first and second intervals are overlapping.

14. The portable spirometer according to claim 1, wherein at least one of the heating element, the temperature sensor and the reference temperature sensor is positioned within the conduit.

15. A method of measuring the flow of air being inhaled or exhaled by a user, comprising:
blowing air into a mouthpiece being releasably connected to a housing,
forwarding part of the air from a main flow channel of the mouthpiece to an air conduit of a sensor unit being in fluid communication with the main flow channel of the mouthpiece when connected to said housing, at least a component of the sensor unit being in the air conduit that is separate from the main flow channel and in fluid communication with the main flow channel, where the air conduit is configured to receive at least a part of the flow of the exhaled or inhaled air via the mouthpiece, and
measuring a first measurement of a thermal flow of air flowing in the air conduit by means of the sensor unit, wherein said sensor unit comprises at least one digital differential pressure sensor comprising:
a heating element,
a temperature sensor arranged upstream of the heating element, and
a reference temperature sensor arranged downstream of the heating element,
wherein the first measurement is converted to a value representing air flow through the main flow channel, and
wherein the at least one digital differential pressure sensor measures a first temperature and a second temperature which are converted to a differential pressure.

16. A method according to claim 15, wherein one or more characteristics of the flow of exhaled or inhaled air is measured by measuring a first temperature of a part of the flow by the temperature sensor, heating the part of the air having past the temperature sensor by means of the heating element, and measure a second temperature of the part of the flow by the reference temperature sensor.

* * * * *